(12) United States Patent
Douglas et al.

(10) Patent No.: US 9,689,850 B2
(45) Date of Patent: Jun. 27, 2017

(54) MANAGING ATMOSPHERIC CONDITIONS OF A TEST COMPUTING DEVICE

(71) Applicant: Oracle International Corporation, Redwood City, CA (US)

(72) Inventors: David Douglas, Palo Alto, CA (US); Anthony Eberhardt, Los Gatos, CA (US); Henry Bono, San Jose, CA (US); Yuan Gao, Sunnyvale, CA (US)

(73) Assignee: Oracle International Corporation, Redwood Shores, CA (US)

( * ) Notice: Subject to any disclaimer, the term of this patent is extended or adjusted under 35 U.S.C. 154(b) by 401 days.

(21) Appl. No.: 14/315,256

(22) Filed: Jun. 25, 2014

(65) Prior Publication Data

US 2015/0377505 A1 Dec. 31, 2015

(51) Int. Cl.
| | | |
|---|---|---|
| *F24F 11/00* | (2006.01) | |
| *G05B 15/02* | (2006.01) | |
| *G01N 33/00* | (2006.01) | |
| *H05K 7/20* | (2006.01) | |

(52) U.S. Cl.
CPC ..... *G01N 33/0016* (2013.01); *G01N 33/0073* (2013.01); *G05B 15/02* (2013.01); *H05K 7/20745* (2013.01)

(58) Field of Classification Search
CPC . G06F 1/20; G06F 2200/201; H05K 7/20736; H05K 7/20745; H05K 7/20827; H05K 7/20836; H05K 7/20709; H05K 7/20718; H05K 7/20754; F24F 11/0012; F24F 11/008; F24F 13/02; F24F 13/08; F24F 2011/0041; F24F 2011/0042; F24F 3/00; F24F 11/00; F24F 13/00; G01N 33/0016; G01N 33/00; G01N 33/0073; F25B 49/00
See application file for complete search history.

(56) References Cited

U.S. PATENT DOCUMENTS

| | | | | |
|---|---|---|---|---|
| 2007/0074525 | A1* | 4/2007 | Vinson | H05K 7/20745 62/259.2 |
| 2012/0171943 | A1* | 7/2012 | Dunnavant | H05K 7/20745 454/184 |

FOREIGN PATENT DOCUMENTS

JP 2010-160076 * 7/2010 ............ G01N 17/00

OTHER PUBLICATIONS

"Power and cooling technologies in the HP POD 240a"; www.hp.com/go/pod240a; Copyright 2012 Hewlett-Packard Development Company, LP. (8 pages).

Atwood, Don, et al., "Reducing Data Center Cost with an Air Economizer", Intel Corporation, Aug. 2008, (4 pages).

Evans, Tony, "The Different Types of Air Conditioning Equipment for IT Environments", White Paper #59, Rev 2004-0, American Power Conversion. 2004 (21 pages).

* cited by examiner

*Primary Examiner* — Daniel S Larkin
(74) *Attorney, Agent, or Firm* — Osha Liang LLP

(57) ABSTRACT

A system for controlling an atmospheric condition. The system includes: a pre-atmospheric conditioner configured to: collect ambient air and generate test air comprising the atmospheric condition for a first test computing device by modifying the ambient air. The system also includes an intake conduit, external to the first test computing device, configured to channel the test air to the first test computing device.

18 Claims, 4 Drawing Sheets

MANAGING ATMOSPHERIC CONDITIONS OF A TEST COMPUTING DEVICE

CROSS-REFERENCE TO RELATED APPLICATIONS

The subject matter of the present application may be related to the subject matter of U.S. patent application Ser. No. 14/315,253, now U.S. Pat. No. 9,632,068, filed on Jun. 25, 2014, and entitled: "SETTING ATMOSPHERIC CONDITIONS OF A TEST COMPUTING DEVICE."

BACKGROUND

In the field of networking, testing of network devices, such as servers, in different operational environments with varying atmospheric conditions is conducted in temperature controlled rooms, including data centers, chambers, and wind tunnels. Creating the environmental test or operating conditions in the temperature controlled rooms is typically expensive.

SUMMARY

In general, in one aspect, the invention relates to a system for controlling an atmospheric condition. The system comprises: a pre-atmospheric conditioner configured to: collect ambient air; and generate test air comprising the atmospheric condition for a first test computing device by modifying the ambient air; and an intake conduit, external to the first test computing device, configured to channel the test air to the first test computing device.

In general, in one aspect, the invention relates to a system for controlling an atmospheric condition. The system comprises: a plurality of production computing devices in a room; a first test computing device in the room; a pre-atmospheric conditioner configured to generate test air comprising the atmospheric condition for the first test computing device by modifying ambient air; and an intake conduit, external to the first test computing device, configured to: channel the test air to the first test computing device; and environmentally separate the plurality of production computing devices from the test air.

In general, in one aspect, the invention relates to a method for controlling an atmospheric condition. The method comprises: obtaining, by a pre-atmospheric conditioner, ambient air from a facility comprising a first test computing device; generating, by the pre-atmospheric conditioner, test air comprising the atmospheric condition by modifying the ambient air; and channeling, by an intake conduit external to the first test computing device, the test air to the first test computing device.

Other aspects of the invention will be apparent from the following description and the appended claims.

DETAILED DESCRIPTION

Figure 1:
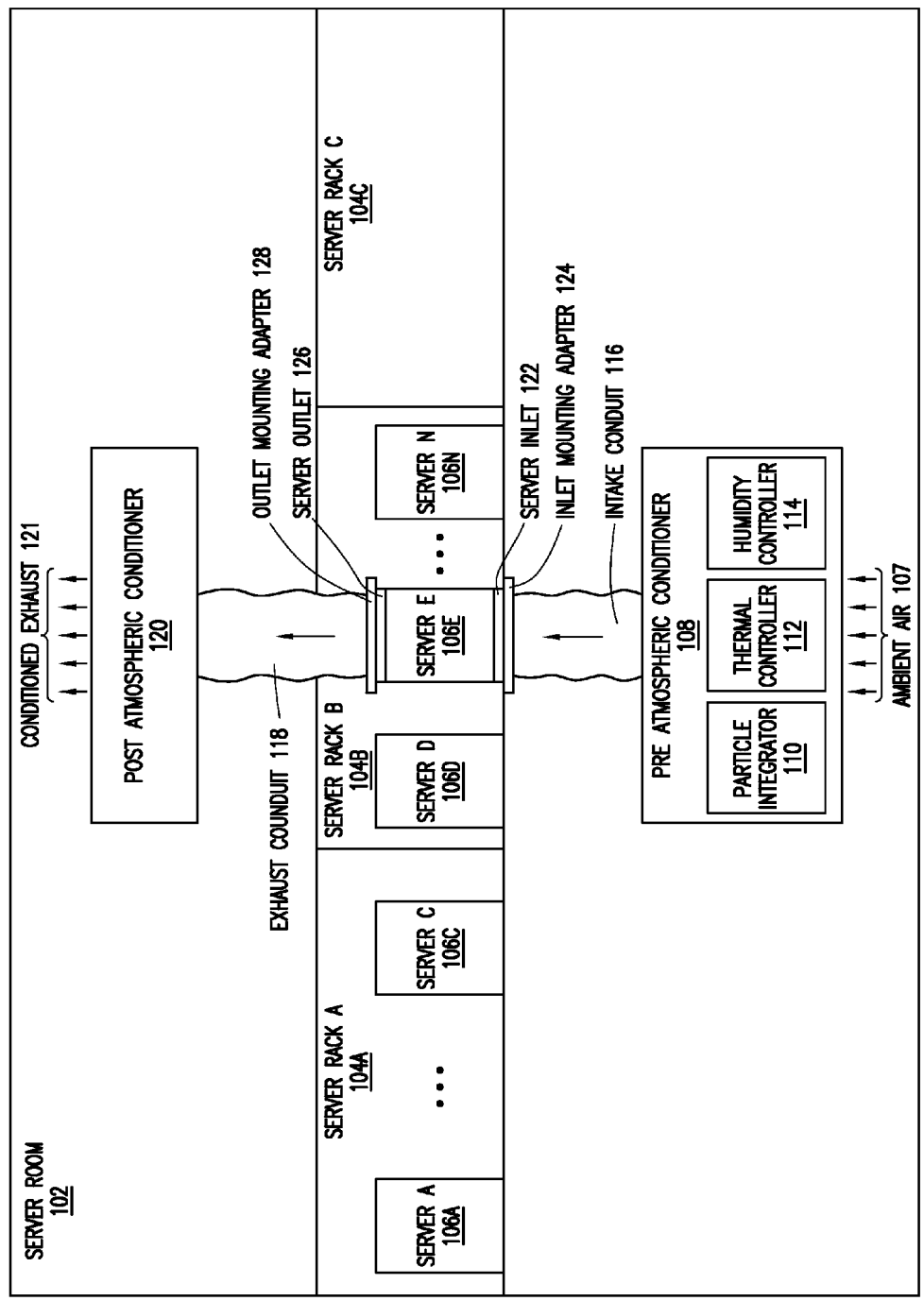
FIG. 1 shows a system for setting/controlling atmospheric conditions for a test computing device in a facility also having a production computing device(s) in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a method and system for managing atmospheric conditions for a test computing device. Specifically, one or more pre-atmospheric conditioners collect ambient air in a facility (e.g., server room) in which the test computing device is situated. The pre-atmospheric conditioner(s) generate test air having the desired atmospheric conditions (e.g., temperature, moisture, pressure, chemical content, etc.) by modifying the collected ambient air. An intake conduit then channels the test air to the test computing device in accordance with one or more embodiments of the invention. Further, embodiments of the invention include an exhaust conduit that channels the exhaust of the test computing device to one or more post-atmospheric conditioners. The post-atmospheric conditioner(s) generate conditioned exhaust having the same or approximately the same atmospheric conditions (e.g., temperature, moisture, pressure, chemical content, etc.) as the ambient air in the facility. The test computing device may be located in the same facility (e.g., server room or any room having a computing device(s)) as other computing devices. The intake conduit, exhaust conduit, the pre-atmospheric conditioner(s), and/or the post-atmospheric conditioner(s) environmentally separate (e.g., thermally isolate) the other computing devices from the generated test air and the exhaust. Accordingly, the other computing devices can remain in the same facility as the test computing device and operate normally even though the test computing device is being subjected to test air. In general, the methods/systems for controlling the test environment may also be applied to operating environments.

FIG. 1 shows a system in accordance with one or more embodiments of the invention. As shown in FIG. 1, there exists a server room (102). The server room (102) includes one or more server racks (e.g., server rack A (104A), server rack B (104B), server rack C (104C)). Each server rack is a shelf configured to mount one or more servers. For example, server rack A (104A) mounts server A (106A) and server C (106C), server rack B (104B) mounts server D (106D), server E (106E), and server N (106N), and server rack C (104C) does not mount any servers. Two server racks may be kept in close proximity to each other or may even be connected. For example, server rack A (104A) is connected to server rack B (104B). Server rack B (104B) is connected to server rack C (104C).

In one or more embodiments of the invention, a server is any type of physical system that includes persistent storage (e.g., hard disk), memory (e.g., Random Access Memory), one or more processors, and one or more network interfaces (not shown). In one or more embodiments of the invention, a processor may be an integrated circuit for processing instructions. For example, the processor(s) may be one or more cores, or micro-cores of a processor. In one or more embodiments of the invention, a network interface on a server is the medium through which communication of data to another network interface on a network device (e.g., server, switch, and router) is possible.

In FIG. 1, server E (106E) is a test computing device. In other words, server E (106E) is being subjected to test air that has different atmospheric conditions (e.g., temperature, pressure, humidity, oxygen content, dust particles, etc.) than the air of the server room (102). The performance of server E (106E) is being observed, measured, evaluated, etc. while being exposed to the test air. Server A (106A), server C (106C), server D (106D), and server N (106N) are not under test and may be operating normally while exposed to the air of the server room (102), referred to as ambient air (107). Accordingly, each of server A (106A), server C (106C), server D (106D), and server N (106N) may be referred to as a production computing device.

Still referring to FIG. 1, server E (106E) includes a server outlet (126) and a server inlet (122). The server outlet (126) expels exhaust from server E (106E). Server E (106E) may include one or more fans to expel exhaust from server E (106E) through the server outlet (126). The server inlet (122) is a portal through which air flows into the server. Server E (106E) may include one or more fans to draw air into server E (106E). The server inlet (122) and the server outlet (126) may correspond to vents, grates, or openings in the case/shell of server E (106E).

In one or more embodiments of the invention, there exists a pre-atmospheric conditioner (108). The pre-atmospheric conditioner (108) includes a user interface that allow users (i.e., server testers, network administrators, lab technicians, etc.) to select (i.e., set, input, program, specify, etc.) the desired atmospheric conditions of the test air for server E (106E). For example, using the user interface, the test air may be set to 30° F. with 30% humidity. The pre-atmospheric conditioner (108) is configured to generate test air with the selected atmospheric conditions using ambient air (107) in the server room (102). Specifically, the pre-atmospheric conditioner (108) controls/modifies the atmospheric conditions (e.g., temperature, moisture, pressure, chemical composition, etc.) of the collected ambient air (107) to generate the test air with the selected atmospheric conditions. In other words, the pre-atmospheric conditioner (108) transforms the collected ambient air (107) into the desired test air.

The pre-atmospheric conditioner (108) may include a particle integrator (110), a thermal controller (112), and a humidity controller (114). In one or more embodiments of the invention, the pre-atmospheric conditioner (108) may include additional modules to modify atmospheric conditions of the ambient air (107) to generate test air. For example, a gas module (not shown) may decrease the oxygen content and increase the nitrogen content of the ambient air (107) to generate test air that mimics atmospheric conditions at a high altitude.

In one or more embodiments of the invention, the particle integrator (110) is any combination of hardware and/or software that includes functionality to introduce dust particles into the ambient air (107). For example, the particle integrator may correspond to a vent through which dust particles may be added by a user (e.g., server tester and network administrator). As another example, the particle integrator may correspond to a container of dust that automatically dispenses dust particles to the ambient air (107). In one or more embodiments of the invention, any type of particle may be introduced into the exhaust by the pre-atmospheric conditioner (108). Examples of particles include sand, clay, silt, etc.

In one or more embodiments of the invention, the thermal controller (112) is any combination of hardware and/or software that includes functionality to modify the temperature of the ambient air (107). For example, the thermal controller may include an air conditioner to cool the ambient air (107) or a heater to heat the ambient air. The thermal controller (112) may include a thermometer to measure the ambient air (107) at any stage as it is transformed into the test air.

In one or more embodiments of the invention, the humidity controller (114) is any combination of hardware and/or software that includes functionality to modify (e.g., increase or decrease) the moisture content of the ambient air (107). In one or more embodiments of the invention, the humidity controller (114) may correspond to a system that increases moisture content of the ambient air (107). For example, a humidifier may be used to add and maintain a set percentage for the moisture content. In one or more embodiments of the invention, the humidity controller (114) may correspond to a system that decreases moisture content of the ambient air (107). For example, a dehumidifier may be used to remove moisture and maintain a set percentage for the moisture content.

In one or more embodiments of the invention, the test air generated by the pre-atmospheric conditioner (108) is delivered to server E (106E) by an intake conduit (116) and an inlet mounting adapter (124). The intake conduit (116) is effectively a tube, having any type/size of cross-section, that channels the ambient air (107) in the server room (102) to the pre-atmospheric conditioner (108). The intake conduit (116) may be constructed with any type of material that environmentally separates (e.g., thermally isolates) the test air from the server room (102) and the other servers (e.g., server A (106A), server C (106C), server D (106D), and server N (106N)). The inlet mounting adapter (124) connects the intake conduit (116) to the server inlet (122). For example, the inlet mounting adapter (124) may correspond to an adhesive, such as tape or glue that attaches the intake conduit (116) directly to the server inlet (122). The inlet mounting adapter may be an interface that connects the shape/size of the intake conduit (116) with the shape/size of the server inlet (122).

In one or more embodiments of the invention, there also exists a post-atmospheric conditioner (120). The post-atmospheric conditioner (120) includes a user interface that allow users (i.e., server testers, network administrators, lab technicians, etc.) to select (i.e., set, input, program, specify, etc.) the desired atmospheric conditions of the conditioned exhaust (121). For example, using the user interface, the conditioned exhaust (121) may be set to 68° F. with 10% humidity. The post-atmospheric conditioner (120) is configured to generate conditioned exhaust (121) by modifying the exhaust expelled by server E (106E) before it is released into the server room (102). Specifically, the post-atmospheric conditioner (120) controls/modifies the atmospheric conditions (e.g., temperature, moisture, pressure, chemical composition, etc.) of the exhaust to generate the conditioned exhaust (121) with atmospheric conditions that mimic/resemble/match the atmospheric conditions of the ambient air (107). In other words, the post-atmospheric conditioner modifies the exhaust to generate/release conditioned exhaust that matches or is similar to the ambient air.

In one or more embodiments of the invention, the post-atmospheric conditioner (120) includes one or more of the modules (e.g., particle integrator, thermal controller, and humidity controller) described above in the pre-atmospheric conditioner (108). In one or more embodiments of the invention, the post-atmospheric conditioner (120) may include any module that modifies atmospheric conditions of the exhaust. For example, the percentage of gases in the exhaust may be modified by a gas module. In one or more embodiments of the invention, the post-atmospheric conditioner (120) is optional. Said another way, modification of the exhaust by the post-atmospheric conditioner (120) may not be needed. The exhaust is then released to the server room (102).

In one or more embodiments of the invention, the post-atmospheric conditioner (120) is connected to the server outlet (126) by an exhaust conduit (118) and an outlet mounting adapter (128). The exhaust conduit (118) is effectively a tube, having any type/size of cross-section, that channels the exhaust expelled by server E (106E) to the post-atmospheric conditioner. The exhaust conduit may be constructed with any type of material that environmentally separates the exhaust from the server room (102) and the other servers (e.g., server A (106A), server C (106C), server D (106D) and server N (106N)). The outlet mounting adapter (128) connects the exhaust conduit (118) to the server outlet (126). For example, the outlet mounting adapter may correspond to an adhesive, such as tape or glue that attaches the exhaust conduit (118) directly to the server outlet (126). The outlet mounting adapter may be an interface that connects the shape/size of the exhaust conduit (118) with the shape/size of the server outlet (126).

While FIG. 1 shows a configuration of components, other configurations may be used without departing from the scope of the invention. For example, various components may be combined to create a single component. As another example, the functionality performed by a single component may be performed by two or more components. Moreover, although embodiments of the invention have focused heavily on severs (106A-106N), those skilled in the art, having the benefit of this detailed description, will appreciate that any type of computing device (e.g., personal computer (PC), laptop, mainframe, smart phone, personal digital assistant, cable box, kiosk, printer, tablet PC, e-reader, monitor, fax machine, copier, oscilloscope, electronic test instrument, etc.) may also be used. Further, although embodiments of the invention have focused on a server room (102), those skilled in the art, having the benefit of this detailed description, will appreciate the test computing device(s) and production computing device(s) may be located in any type of facility.

Figure 2:
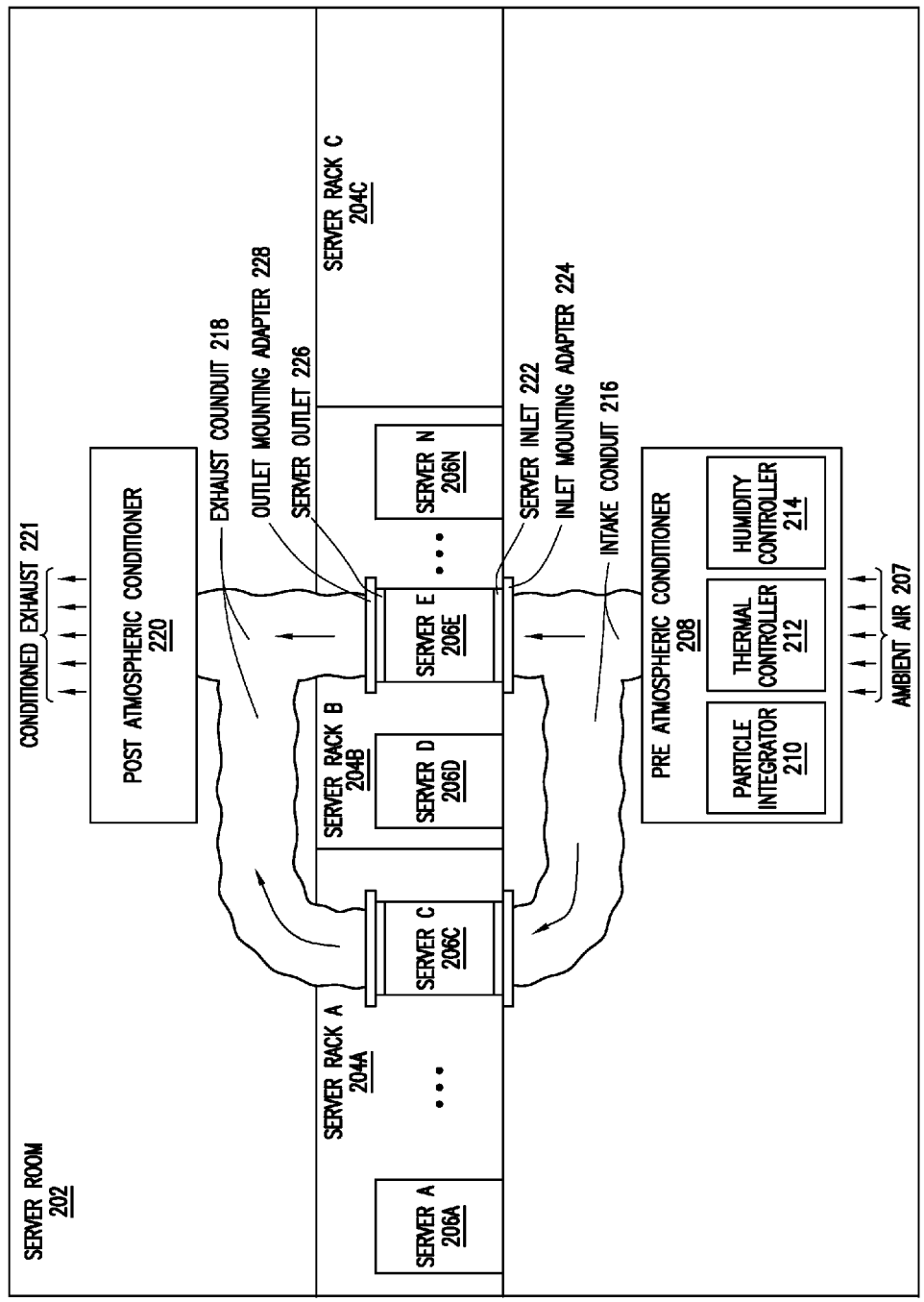
FIG. 2 shows a system for setting/controlling atmospheric conditions for multiple test computing devices in a facility also having a production computing device(s) in accordance with one or more embodiments of the invention in accordance with one or more embodiments of the invention.

FIG. 2 shows a system in accordance with one or more embodiments of the invention. As shown in FIG. 2, there exists a server room (202). The server room (202) is essentially the same as the server room (102) discussed above in reference to FIG. 1. One or more server racks (e.g., server rack A (204A), server rack B (204B)) in server room (202) are essentially the same as the one or more server racks (e.g., server rack A (104A), server rack B (104B)) discussed above in reference to FIG. 1. One or more servers (e.g., server A (206A), server B (206B), server C (206C), and server N (206N)) on the server racks are essentially the same as the one or more servers (e.g., server A (106A), server B (106B), server C (106C), server N (106N)) discussed above in reference to FIG. 1.

In FIG. 2, server C (206C) and server E (206E) are test computing devices. In other words, server C (206C) and server E (206E) are subjected to test air that has different atmospheric conditions (e.g., temperature, pressure, humidity, oxygen content, dust particles, etc.) than the air of the server room (202). The performance of server C (106C) and server E (106E) are observed, measured, evaluated, etc. while being exposed to the test air. Server A (206A), server D (206D), and server N (206N) are not under test and may be operating normally while exposed to the air of the server room (202). Accordingly, each of server A (206A), server D (206D), and server N (206N) may be referred to as a production computing device.

Still referring to FIG. 2, a server outlet (226), a server inlet (222), an outlet mounting adapter (228), and an inlet mounting adapter (224) are essentially the same as the server outlet (126), the server inlet (122), the outlet mounting adapter (128), and the inlet mounting adapter (124) discussed above in reference to FIG. 1. Like server E (206E), server C (206C) may also have and/or be connected to a server outlet, a server inlet, an outlet mounting adapter, and an inlet mounting adapter.

In one or more embodiments of the invention, the pre-atmospheric conditioner (208), the particle integrator (210), the thermal controller (212), and the humidity controller (214) are essentially the same as the pre-atmospheric conditioner (108), the particle integrator (110), the thermal controller (112), and the humidity controller (114) discussed above in reference to FIG. 1.

In one or more embodiments of the invention, the test air generated by the atmospheric conditioner(s) is delivered to server C (206C) and server E (206E) by an intake conduit (216). Specifically, the intake conduit (216) branches, with one branch connecting to the server inlet of server C (206C) and the other branch connecting to the server inlet (222) of server E (206E). Except for the branching, the intake conduit (216) is essentially the same as the intake conduit (116), discussed above in reference to FIG. 1.

In one or more embodiments of the invention, there also exists a post-atmospheric conditioner (220). The post-atmospheric conditioner (220) is configured to generate conditioned exhaust (221) by modifying the exhaust expelled by server C (106C) and server E (106E) before it is released into the server room (202). The post-atmospheric conditioner (220) is essentially the same as the post-atmospheric conditioner (120) discussed above in reference to FIG. 1.

In one or more embodiments of the invention, the post-atmospheric conditioner (120) is connected to the exhaust conduit (218). Specifically, the exhaust conduit (208) branches, with one branch connecting to the server outlet of server C (206C) and the other branch connecting to the server outlet (226) of server E (206E). Except for the branching, the exhaust conduit (218) is essentially the same as the exhaust conduit (118), discussed above in reference to FIG. 1.

While FIG. 2 shows a configuration of components, other configurations may be used without departing from the scope of the invention. For example, various components may be combined to create a single component. As another example, the functionality performed by a single component may be performed by two or more components. Further, although embodiments of the invention have focused heavily on severs (206A-206N), those skilled in the art, having the benefit of this detailed description, will appreciate that any type of computing device (e.g., personal computer (PC), laptop, mainframe, smart phone, personal digital assistant, cable box, kiosk, printer, tablet PC, e-reader, monitor, fax machine, copier, oscilloscope, electronic testing instrument, etc.) may also be used. Further still, although FIG. 2 only shows two test computing devices and thus two branches in the intake conduit (216) and the exhaust conduit (218), in other embodiments, any number of test computing devices, and thus any number of branches, may be present.

Figure 3:
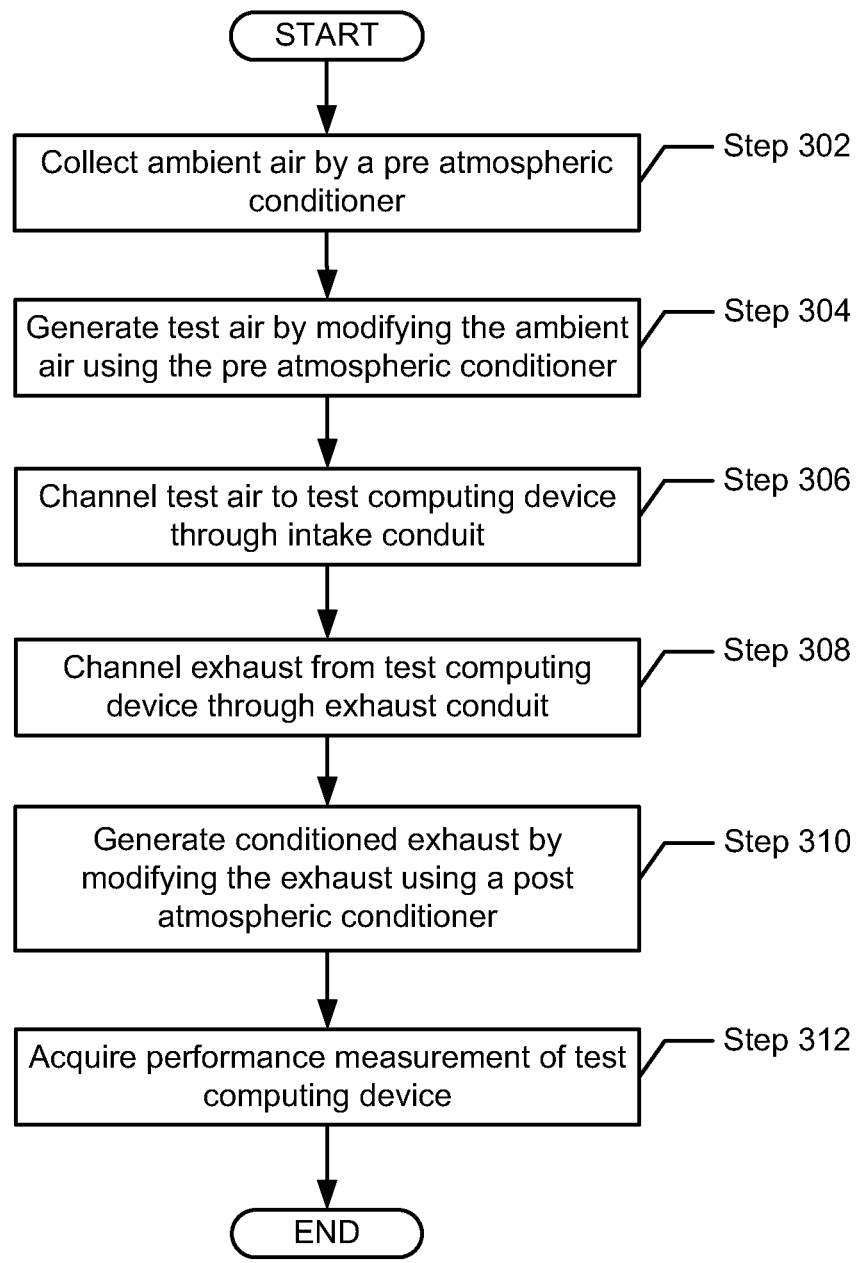
FIG. 3 shows a flowchart for setting/controlling atmospheric conditions for one or more test computing devices in accordance with one or more embodiments of the invention.

FIG. 3 shows a flowchart in accordance with one or more embodiments of the invention. The process depicted in FIG. 3 may be used to set/control the atmospheric conditions for one or more test computing devices. One or more of the steps in FIG. 3 may be performed by one or more of the components discussed above in reference to FIG. 1 and/or FIG. 2. Further, one or more of the steps shown in FIG. 3 may be omitted, repeated, and/or performed in a different order than the order shown in FIG. 3. Accordingly, the scope of the invention should not be considered limited to the specific arrangement of steps shown in FIG. 3.

Initially, ambient air is collected by a pre-atmospheric conditioner (Step 302). In one or more embodiments of the invention, ambient air in a facility (e.g., room) is collected through one or more openings in the pre-atmospheric conditioner. The opening allows air to flow into the pre-atmospheric conditioner, but does not allow air to flow out of the pre-atmospheric conditioner into the facility. For example, a fan or vent may be used by the pre-atmospheric conditioner to intake ambient air from a room.

In Step 304, test air is generated by modifying the ambient air using the pre-atmospheric conditioner in accordance with one or more embodiments of the invention. Once ambient air enters the pre-atmospheric conditioner, the pre-atmospheric conditioner may generate the test air by modifying the atmospheric conditions (e.g., temperature, moisture, pressure, etc.) of the ambient air. In one or more embodiment of the invention, users (i.e., server testers, network administrators, lab technicians, etc.) may operate a user interface on the pre-atmospheric conditioner to select (i.e., set, input, program, specify, etc.) the desired atmospheric conditions of the test air.

Still referring to Step 304, the pre-atmospheric conditioner may modify the atmospheric conditions of the ambient air by modifying the temperature of the exhaust using a thermal controller. For example, the ambient air may be at a temperature of 67° F. To generate test air with a temperature of 85° F., the temperature controller heats the ambient air until a temperature of 85° F. is reached.

Still referring to Step 304, the pre-atmospheric conditioner may generate test air by modifying the moisture content of the ambient air using a humidity controller. For example, the ambient air may have a moisture content of 8%. To generate test air with a moisture content of 30%, the humidity controller adds moisture to the ambient air until a moisture content of 30% is reached. Further, the pre-atmospheric conditioner may generate test air by introducing dust particles into the ambient air. For example, the dust particles in the ambient air may be 35 $\mu g/m^3$. To generate test air with 100 $\mu g/m^3$ of dust particles, the particle integrator may release dust into the ambient air until a measurement of 100 $\mu g/m^3$ is attained.

Still referring to Step 304, the pre-atmospheric conditioner may generate test air by modifying pressure of the ambient air. In one or more embodiments of the invention, the pre-atmospheric conditioner may include fans to accelerate or decelerate the ambient air. For example, the ambient air has a pressure of 100 kPa. To generate test air with a pressure of 150 kPa, fans that flow with the flow of the ambient air may be used to accelerate the ambient air to increase pressure of the ambient air to 150 kPa. Finally, the pre-atmospheric conditioner may generate test air by modifying the composition of gases in the ambient air. For example, the ambient air is composed of 21% oxygen. To generate the test air with 40% oxygen, oxygen may be added (e.g., by accessing an oxygen tank or store). In one or more embodiments of the invention, a combination of the mechanisms to modify atmospheric conditions of the exhaust may be used to generate test air. For example, moisture content and temperature may be modified to generate test air.

In Step 306, test air is channeled to the test computing device through the intake conduit in accordance with one or more embodiments of the invention. The test air that exits from the pre-atmospheric conditioner enters the intake conduit. The intake conduit keeps the test air environmentally separated from the ambient air of the facility in which the test computing device is situated and environmentally separated from any other computing device (e.g., production computing device) in close proximity to the test computing device. In one or more embodiments of the invention, additional devices (e.g., fans) within the intake conduit may be used to propel the test air from the pre-atmospheric conditioner to the test computing device.

In Step 308, exhaust is channeled from the test computing device through an exhaust conduit in accordance with one or more embodiments of the invention. The exhaust conduit keeps exhaust from the test computing device environmentally separated from the ambient air of the room in which the test computing device is situated (e.g., server room, datacenter) and any other computing devices that are in close proximity to the test computing device. In one or more embodiments of the invention, the test computing device outlet propels the exhaust through the exhaust conduit to a post-atmospheric conditioner. In one or more embodiments of the invention, additional devices (e.g., fans) within the exhaust conduit (if used) may be used to propel the exhaust from the test computing device to a post-atmospheric conditioner.

In Step 310, conditioned exhaust is generated by modifying the exhaust using a post-atmospheric conditioner, in accordance with one or more embodiments of the invention. The post-atmospheric conditioner may modify the exhaust using essentially the same mechanisms of the pre-atmospheric conditioner described above in Step 304 (e.g., modify temperature using thermal controller, modify moisture content using humidity controller, etc.). The post-atmospheric conditioner may generate conditioned exhaust by removing particles from exhaust. In one or more embodiments of the invention, the post-atmospheric conditioner may include an air filter to filter and remove dust particles from the exhaust. For example, the exhaust has 100 $\mu g/m^3$. To generate conditioned exhaust with 50 $\mu g/m^3$ of dust particles, an air filter that is capable of removing up to 60 $\mu g/m^3$ of dust particles may be used to remove approximately 50 $\mu g/m^3$ of dust particles. In one or more embodiments of the invention, conditioned exhaust is air with atmospheric conditions that are identical to, or at least similar to, the atmospheric conditions of the ambient air in the facility.

In Step 312, a performance measurement of the test computing device is acquired in accordance with one or more embodiments of the invention. The performance measurement may correspond to the speed of the test computing device, the number of calculations performed by the test computing device, the heat generated by the test computing device, or any metric that describes the function of any software and/or hardware of the test computing device. The performance measurement may be acquired by an electronic testing instrument connected to the test computing device. In one or more embodiments of the invention, the performance measurement of the test computing device is acquired once the test computing device is exposed to the test air.

Figure 4:
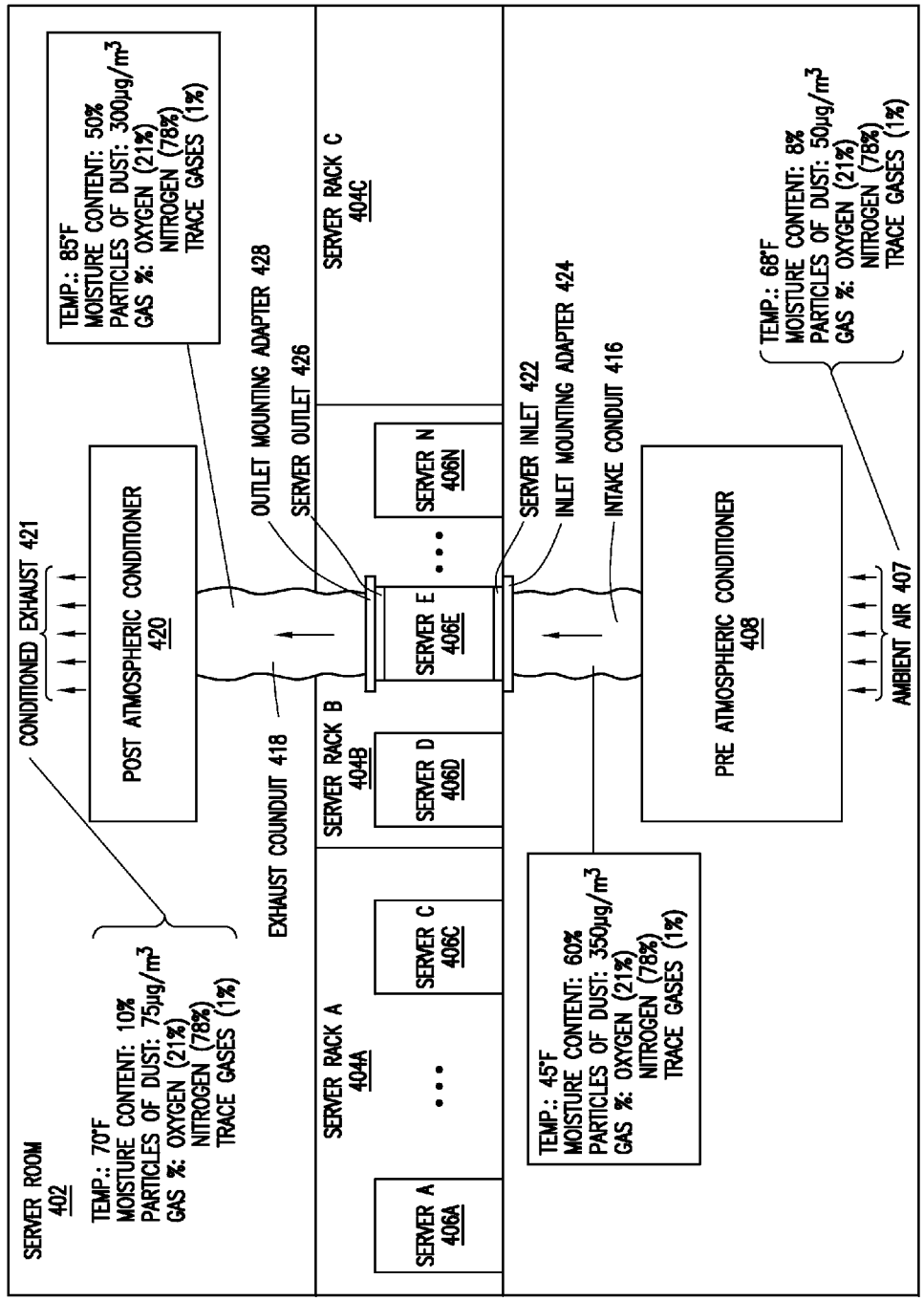
FIG. 4 shows an example of setting/controlling atmospheric conditions for a test computing device in accordance with one or more embodiments of the invention.

FIG. 4 shows an example in one or more embodiments of the invention. The following example is for explanatory purposes only and not intended to limit the scope of the invention.

Referring to FIG. 4, consider a scenario in which ambient air (407) in a server room (402) has the following atmospheric conditions: temperature of 68° F., moisture content of 8%, 50 μg/m³ particles of dust, and gas percentages of 21% oxygen, 78% nitrogen, and 1% trace gases. The server room (402) includes one or more servers (e.g., server A (406A), server C (406C), server D (406D), server E (406E) and server N (406N)). Server A (406A) and server C (406C) are mounted on server rack A (404A). Server E (406E) and server N (406N) are mounted on server rack B (404B). No servers are mounted on server rack C (404C). Server A (406A), server C (406C), server D (406D) and server N (406N) are production computing devices operating in the ambient air (407) of the server room (402). Server E (406E) is a test computing device receiving atmospheric conditions that differ from the ambient air (407) in the server room (402).

Continuing with the example in FIG. 4, ambient air (407) is collected by a pre-atmospheric conditioner (408). The pre-atmospheric conditioner (408) modifies the ambient air (407) to generate the test air. The pre-atmospheric conditioner (408) is connected to an intake conduit (416). The intake conduit (416) is connected to a server inlet (422) on server E (406E) using an inlet mounting adapter (424). The test air may then flow from the pre-atmospheric conditioner (408) through the intake conduit (416) into server E (406E). Thus, server E (406E) is exposed to the atmospheric conditions of the test air from the intake conduit (416).

The test air in the intake conduit (416) has the following atmospheric conditions: temperature of 45° F., moisture content of 60%, 350 μg/m³ particles of dust, and gas percentages of 21% oxygen, 78% nitrogen, and 1% trace gases. The thermal controller in the pre-atmospheric conditioner (408) cooled the temperature of the collected ambient air (407) from 68° F. to 45° F. The humidity controller in the pre-atmospheric conditioner (408) increased the moisture content of the exhaust from 8% to 60%. Finally, the particle integrator in the pre-atmospheric conditioner (408) introduced dust particles to reach 350 μg/m³. The test air in the intake conduit (416) has different atmospheric conditions than the ambient air (407) in the server room (402). This is due to the environmental separation of the test air by the intake conduit (416) from the ambient air (407) and the other servers (406A, 406C, 406D, and 406N).

The server outlet (426) of server E (406E) is connected to an exhaust conduit (418) using an outlet mounting adapter (428). Exhaust from server E (406E) channels through the exhaust conduit (418). The exhaust in the exhaust conduit (418) has the following atmospheric conditions: temperature of 85° F., moisture content of 50%, 300 μg/m³ particles of dust, and gas percentages of 21% oxygen, 78% nitrogen, and 1% trace gases. The temperature of the exhaust is higher (85° F.) due to heat produced by server E (406E). The atmospheric conditions in the exhaust conduit (418) differ from the ambient air (407). Moreover, the exhaust conduit (418) environmentally separates the exhaust from the ambient air and the other servers (406A, 406C, 406D, and 406N).

Exhaust in the exhaust conduit (418) enters a post-atmospheric conditioner (420). The post-atmospheric conditioner (420) modifies the exhaust to generate conditioned exhaust (421). The conditioned exhaust (421) is then released into the server room (402). The conditioned exhaust (421) released by the post-atmospheric conditioner has the following atmospheric conditions: temperature of 70° F., moisture content of 10%, 75 μg/m³ particles of dust, and gas percentages of 21% oxygen, 78% nitrogen, and 1% trace gases. The thermal controller in the post-atmospheric conditioner (420) cooled the temperature of the exhaust from 85° F. to 70° F. The humidity controller in the pre-atmospheric conditioner (420) decreased the moisture content of the exhaust from 50% to 10%. Finally, the particle remover in the post-atmospheric conditioner (420) removed dust particles to reach 75 μg/m³. The atmospheric conditions of the conditioned exhaust (421) are modified by the post-atmospheric conditioner (420) to be closer in value to the atmospheric conditions of the ambient air (407) compared to the atmospheric conditions of the exhaust.

Embodiments of the invention enable the control of atmospheric conditions within one or more test computing devices in a room that also includes one or more production computing devices. Embodiments of the invention channel test air to the test computing device and isolate the test air from the production computing devices. Therefore, embodiments of the invention prevent disruption of the production computing devices by the test air.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for controlling an atmospheric condition, comprising:
    a pre-atmospheric conditioner configured to:
        collect ambient air; and
        generate test air comprising the atmospheric condition for a first test computing device by modifying the ambient air, wherein the pre-atmospheric conditioner comprises a particle integrator configured to introduce a plurality of dust particles to the ambient air;
    an intake conduit, external to the first test computing device, configured to channel the test air to the first test computing device; and
    an inlet mounting adapter connecting an inlet of the first test computing device to the intake conduit.

2. The system of claim 1, wherein the intake conduit channels the test air to a second test computing device.

3. The system of claim 1, wherein the pre-atmospheric conditioner comprises:
    a thermal controller configured to modify a temperature of the ambient air; and
    a humidity controller configured to modify a moisture content of the ambient air.

4. The system of claim 1, wherein the atmospheric condition comprises at least one selected from a group consisting of a temperature, a plurality of dust particles, a moisture content, a pressure, and a composition of a plurality of gases.

5. The system of claim 1, further comprising:
    an exhaust conduit, external to the first test computing device, configured to channel exhaust from the first test computing device; and
    a post-atmospheric conditioner, external to the first test computing device, configured to generate conditioned exhaust by modifying the exhaust.

6. The system of claim 5, wherein the exhaust conduit channels exhaust from a second test computing device to the post-atmospheric conditioner.

7. The system of claim 5, further comprising:
an outlet mounting adapter connecting an outlet of the first test computing device to the exhaust conduit.

8. The system of claim 5, wherein the post-atmospheric conditioner comprises at least one selected from a group consisting of a particle remover, a thermal controller, and a humidity controller.

9. A system for controlling an atmospheric condition, the system comprising:
a plurality of production computing devices in a room;
a first test computing device in the room;
a pre-atmospheric conditioner configured to generate test air comprising the atmospheric condition for the first test computing device by modifying ambient air; and
an intake conduit, external to the first test computing device, configured to:
channel the test air to the first test computing device; and
isolate the plurality of production computing devices from the test air.

10. The system of claim 9, further comprising:
a second test computing device, wherein the intake conduit is further configured to channel the test air to the second test computing device.

11. The system of claim 9, wherein the pre-atmospheric conditioner comprises:
a particle integrator configured to introduce a plurality of dust particles to the ambient air;
a thermal controller configured to modify a temperature of the ambient air; and
a humidity controller configured to modify a moisture content of the ambient air.

12. The system of claim 9, further comprising:
an exhaust conduit, external to the first test computing device, configured to:
channel exhaust from the first test computing device; and
isolate the plurality of production computing devices from the exhaust of the first test computing device; and
a post-atmospheric conditioner, external to the first test computing device and the plurality of production computing devices, configured to generate conditioned exhaust by modifying the exhaust.

13. The system of claim 12, wherein the exhaust conduit is further configured to:
channel exhaust from a second computing device to the post-atmospheric conditioner; and
isolate the plurality of production computing devices from the exhaust of the second test computing device.

14. A method for controlling an atmospheric condition, the method comprising:
obtaining, by a pre-atmospheric conditioner, ambient air from a facility comprising a first test computing device, wherein the pre-atmospheric conditioner comprises a particle integrator configured to introduce a plurality of dust particles to the ambient air;
generating, by the pre-atmospheric conditioner, test air comprising the atmospheric condition by modifying the ambient air;
channeling, by an intake conduit external to the first test computing device, the test air to the first test computing device; and
acquiring a performance measurement of the first test computing device receiving the test air, wherein the performance measurement is selected from a group consisting of the speed of the first test computing device, the number of calculations performed by the first test computing device, and the heat generated by the first test computing device.

15. The method of claim 14, further comprising:
channeling, by an exhaust conduit external to the first test computing device, exhaust from the first test computing device; and
generating, by a post-atmospheric conditioner external to the first test computing device, conditioned exhaust by modifying the exhaust.

16. The method of claim 15, further comprising:
channeling exhaust from a second test computing device in the facility to the post-atmospheric conditioner.

17. The method of claim 14, further comprising:
channeling the test air to a second test computing device in the facility.

18. The method of claim 14, wherein the atmospheric condition comprises at least one selected from a group consisting of a temperature, a plurality of dust particles, a moisture content, a pressure, and a composition of a plurality of gases.

* * * * *

UNITED STATES PATENT AND TRADEMARK OFFICE
CERTIFICATE OF CORRECTION

PATENT NO. : 9,689,850 B2
APPLICATION NO. : 14/315256
DATED : June 27, 2017
INVENTOR(S) : David Douglas et al.

It is certified that error appears in the above-identified patent and that said Letters Patent is hereby corrected as shown below:

On the Title Page

In the illustrative figure, Ref. Numeral 118, Line 6, labeled "EXHAUST COUNDUIT" should read -- EXHAUST CONDUIT --.

In the Drawings

Fig. 1, Sheet 1 of 4, reference numeral 118 labeled "EXHAUST COUNDUIT" should read -- EXHAUST CONDUIT --.

Fig. 2, Sheet 2 of 4, reference numeral 218 labeled "EXHAUST COUNDUIT" should read -- EXHAUST CONDUIT --.

Fig. 4, Sheet 4 of 4, reference numeral 418 labeled "EXHAUST COUNDUIT" should read -- EXHAUST CONDUIT --.

Signed and Sealed this
Second Day of July, 2019

Andrei Iancu
*Director of the United States Patent and Trademark Office*